United States Patent [19]

Duffin et al.

[11] Patent Number: 4,626,606

[45] Date of Patent: Dec. 2, 1986

[54] PRODUCTION OF HEXANITROSTILBENE (HNS)

[75] Inventors: Henry C. Duffin, Surbiton; Peter Golding, Epping; Asoka M. Jaweera-Bandara, Surbiton, all of England

[73] Assignee: The Secretary of State for Defence in Her Britannic Majesty's Government of the United Kingdom of Great Britain and Northern Ireland, London, England

[21] Appl. No.: 632,294

[22] Filed: Jul. 19, 1984

[30] Foreign Application Priority Data

Jul. 22, 1983 [GB] United Kingdom ................ 8319850

[51] Int. Cl.$^4$ .......................................... C07C 79/10
[52] U.S. Cl. ..................... 568/931; 260/688; 568/928
[58] Field of Search ................. 568/931, 928; 260/688

[56] References Cited

U.S. PATENT DOCUMENTS

| | | | |
|---|---|---|---|
| 2,965,681 | 12/1960 | Stansbury | 568/931 |
| 3,505,413 | 4/1970 | Shipp | 568/931 |
| 3,636,168 | 1/1972 | Josephson | 568/931 |
| 3,716,590 | 2/1973 | Caraculacu et al. | 568/931 |
| 3,895,055 | 7/1975 | Itatani et al. | 568/931 |
| 3,941,853 | 3/1976 | Shipp et al. | 568/931 |
| 4,085,152 | 4/1978 | Salter et al. | 568/931 |
| 4,199,532 | 4/1980 | Angres | 568/931 |
| 4,221,745 | 9/1980 | Gilbert | 568/931 |
| 4,221,746 | 9/1980 | Gilbert | 568/931 |
| 4,238,420 | 12/1980 | Bird et al. | 568/931 |
| 4,238,421 | 12/1980 | Bird et al. | 568/931 |
| 4,243,614 | 1/1981 | Gilbert | 568/931 |
| 4,255,358 | 3/1981 | Jones et al. | 568/931 |
| 4,268,696 | 5/1981 | Sollott et al. | 568/931 |
| 4,270,012 | 5/1981 | Gilbert | 568/931 |
| 4,294,976 | 10/1981 | Itatani et al. | 568/931 |
| 4,307,258 | 12/1981 | Sollott | 568/931 |

FOREIGN PATENT DOCUMENTS

| | | |
|---|---|---|
| 1513221 | 6/1978 | United Kingdom . |
| 1570569 | 7/1980 | United Kingdom . |

OTHER PUBLICATIONS

*Propellants and Explosives,* vol. 3, No. 1, Apr. 2, 1978, pp. 115–120, P. Golding et al., "Studies on the Synthesis of 2,2', 4,4', 4,7'-Hexanitrostilbene".

*Primary Examiner*—Stephen J. Lechert, Jr.
*Assistant Examiner*—Anne Brookes
*Attorney, Agent, or Firm*—Stevens, Davis, Miller & Mosher

[57] ABSTRACT

A process for the manufacture of 2,2', 4,4', 6,6-hexanitrostilbene (HNS) from dipicrylethane (DPE) or trinitrotoluene (TNT) which consists of oxidizing DPE or TNE substrate in the presence of an aprotic solvent and a basic salt of a carboxylic acid. The acid preferably consists of an ammonium or an alkali metal salt of a monocarboxylic or a dicarboxylic acid. The reaction step consists of heating the substrate and salt dissolved in the solvent to between 15° and 50° C., and contacting the reaction mixture with dry air or oxygen for up to 2 hours. The HNS product is precipitated out by quenching the reaction mixture in acidified water, and is optionally purified by washing first in methanol and then in acetone.

32 Claims, No Drawings

PRODUCTION OF HEXANITROSTILBENE (HNS)

This invention relates to the production of 2,2',4,4'6,6'-Hexanitrostilbene (HNS) (also known as 1,2 bis(2,4,6-trinitrophenyl) ethene) either from 2,4,6 trinitrotoluene (TNT) or from 1,2 dipicrylethane (DPE) (also known as 2,2',4,4',6,6' hexanitrobibenzyl (HNBB) and 1,2 bis (2,4,6-trinitrophenyl)ethane). In particular, the invention relates to the production of HNS from DPE.

HNS is a thermally-stable explosive which is especially useful as a crystal-modifying additive in melt-cast TNT. The first unequivocal synthesis of HNS was disclosed in U.S. Pat. No. 3,505,413 (Shipp). This document describes a process for HNS production which is based on the reduction of TNT with sodium hypochlorite in tetrahydrofuran/methanol solution at 15° C. The crude HNS produced is washed in acetone to remove the bulk of coprecipitated impurities. The yield of HNS produced by this process is low, typically only abouyt 30-35%, and the process also produces a large number of unwanted by-products, some of which are difficult to remove from the HNS product and from the recyclable tetrahydrofuran solvent. Later improvements to this process disclosed in UK Pat. Nos. 1513221 and 1570569 increased HNS yields to about 50%.

More recently, Hungarian Pat. No. T/9639 VE-719 (Kompolthy et al) disclosed a further process for the production of HNS which essentially consisted of oxidative coupling of TNT in the presence of air, methanolic potassium hydroxide solution, a polar aprotic solvent and optionally a catalyst consisting of anhydrous copper sulphate or cobalt naphthenate. Furthermore Kompolthy et al disclosed that their process can also be used for the production of the intermediate product DPE from TNT, and of HNS from DPE. Typically, they obtained yields of 30-55% HNS from TNT, though HNS yields of up to 90% from DPE were obtained using an anhydrous copper sulphate/pyridine catalyst. These yields were later generally confirmed by Golding and Hayes (Propellants and Explosives 4, 115-120 (1979)). However, Golding and Hayes also found (by HPLC analysis) that the crude products obtained by the Hungarian process usually contain a large number of unwanted water-insoluble by-products, rendering the extraction of high purity HNS a difficult and costly operation. Furthermore, Golding and Hayes found that the removal of catalyst from the organic product often requires repeated washing with toluene or acetone, and in some cases requires recrystallization of the product for dimethylsulphoxide solvent.

The present inventors have now found that many of the above undesirable side reactions can be avoided if the oxidation of DPE or TNT is conducted in the presence of certain weak organic bases rather than the strong bases (especially potassium hydroxide) and the transition metal catalysts favoured by the Hungarians. This reduction in side reactions generally leads to a corresponding increase in HNS yield.

Accordingly, the present invention provides a method of preparing HNS which comprises the steps of (a) oxidising to HNS a nitrated organic reactant of general formula I,

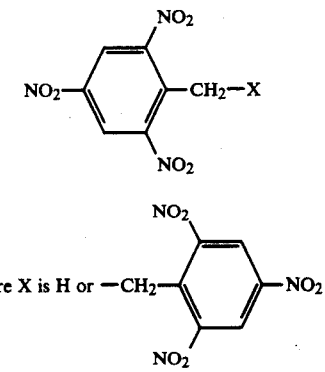

in a reaction medium comprising an aprotic solvent having a salt of a carboxylic acid dissolved therein, and (b) recovering the HNS from the medium.

The nitrated organic reactant of general formula I, which by definition comprises either DPE or TNT, may be oxidised to HNS by optionally substituted quinones, hydrogen peroxide or, which is prefered, by oxygen. The source of oxygen in the oxidation step is preferably gaseous oxygen or air, though using gaseous oxygen does appear to give rise to slightly higher yields of HNS. The oxidation reaction is allowed to proceed to completion (typically after 30 minutes-2 hours) at a temperature which is preferably maintained between 15° C. and 50° C. Where the DPE or TNT reactant is oxidised by oxygen, completion of the oxidation reaction is generally associated with a colour change in the reaction medium to a distinct red/brown.

HNS may be recovered from the reaction medium by techniques known in the art of HNS production. Conveniently, after completion of the oxidation reaction, the reaction medium is mixed with an acidified aqueous solution to precipitate out a crude water-insoluble product containing HNS. The crude product may then be purified by, for example, washing with methanol and/or acetone to remove any nitrated organic reactant (DPE and/or TNT) and any other water insoluble by-product of the reaction. Any DPE and/or TNT thus removed may be recovered by solvent stripping for subsequent reuse if desired.

Unlike the method of Kompolthy et al, the present inventors have found that using the present method, the identity of the aprotic solvent appears to have little effect on the preferred ratios of reactant to catalyst used in the reaction mixture. In general the present inventors have found that, regardless of the aprotic solvent used, HNS yield increases with increasing ratio of basic salt concentration to nitrated organic reactant concentration in the reaction medium, with a corresponding decrease in unreacted nitrated organic reactant in the end product, until beyond a certain optimum ratio of concentrations, by-products yield begins to increase at the expense of HNS yield. The molar ratio of the nitrated organic reactant of general formula I to the basic salt in the reaction medium is preferably between 1:0.5 and 1:10, most preferably between 1:1 and 1:6, giving typical maximum HNS yields of 96 mole % from DPE reactant and of 62 mole % from TNT reactant. Yields of water-insoluble by-products are as low as 0-2% by weight in the crude product when employing DPE as the nitrated organic reactant of general formula I.

The basic salt of the carboxylic acid must be soluble in the aprotic solvent in the presence of the reactants and products of the reaction, and it is preferable also readily soluble in aqueous solution to prevent it from being co-precipitated with the HNS-containing crude product. For this reason the salt is preferably an alkali metal salt or an ammonium salt. Sodium and potassium salts of common carboxylic acids (eg acetic annd formic acid) are generally relatively inexpensive, and so a high rate of recovery of these salts after aqueous quenching of the reaction medium is unnecessary. Lithium salts, although they are generally more expensive than the corresponding sodium and potassium salts, have the advantage of being more soluble in common aprotic solvents. Since the ratio of DPE or TNT reactant to basic salt in the reaction mixture largely determines HNS product yield, clearly the greater the solubility of the basic salt in the mixture the greater will be the potential product output from a reaction medium of a given volume. Ammonium salts appear even more advantageous in this respect, as they are generally even more soluble in the reaction medium than are lithium salt as well as being generally less expensive.

The carboxylic acid may be a monofunctional, difunctional, or polyfunctional acid, and may be aromatic or alipatic. While salts of monocarboxylic acids are, under certain circumstances, found to give rise to exceptionally high yields of HNS which are rarely exceeded when using salts of polyfunctional or difunctional carboxylic acids, these latter salts have the advantage that they tend to decompose the HNS product much more slowly than do salts of monocarboxylic acids. Thus rather than having to quench the oxidation reaction soon after the bulk of the HNS product is formed (indicated, for example, by the colour change in the reaction mixture), when using salts of di- or polyfunctional carboxylic acids (for example oxalates, succinates, citrates, or tartrates) it is possible to leave the reaction mixture for several hours and allow a relatively pure HNS product to crystallise out slowly from the reaction medium. The more rapid crystallisation required after using salts of monocarboxylic acid in the oxidation step leads to a relatively impure product precipitating out. Slow crystallization of HNS also encourages large crystal growth of the product which is thus easier to filter from the reaction mixture than the fine precipitates produced by rapid crystallisation brought about, for example, through rapid quenching in dilute aqueous solution. One further advantage of the use of salts of di- and polyfunctional carboxylic acids is that it allows methods of preparing HNS to be employed which require that the salt and the HNS product remain in intimate contact with one another for considerable periods of time before the HNS is separated from solution, as is often the case with large scale continuous rather than batch methods of preparation. Because they decompose HNS relatively slowly, the use of salts of di- and polyfunctional carboxylic acids may thus assist in increasing the overall yield of HNS when employing continuous methods of HNS production.

Aprotic solvents which are suitable for use in this invention are those in which the reactants are readily dissolved, but which do not undergo chemical reaction themselves during the reaction step. Such solvents are generally entirely miscible with water, and so for convenience the aprotic solvent has a boiling point well above that of water to allow the solvent to be recovered from the water-quenched reaction medium by distilling off the water. Consistently high yields of HNS are obtained, by methods of preparation in accordance with the present invention, using such aprotic solvents as dimethylsulphoxide (DMSO), dimethylformamide (DMF) and hexemethylphosphoramide (HMPA). DMF and DMSO are especially preferred, because they are both cheaper and less carcinogenic than HMPA.

The resent inventors have found one considerable advantage of the present invention is that the reaction medium may additionally contain from 0 to 30% by volume, preferably from 0 to 20% by volume, of a protic solvent during the oxidation step without having a particularly detrimental effect on the yield of HNS. More preferably, the reaction medium may additionally contain from 0 to 15% by volume of the protic solvent, and more preferably it may contain from 0 to 10% by volume of the protic solvent.

Examples of protic solvents which, when dissolved in the reaction medium at the concentrations mentioned above, do not have a particularly detrimental effect on HNS yield are water and alkanols, especially methanol. This finding lends several important advantages to the method of the present invention.

One advantage of this finding is that as the aprotic solvent may contain a relatively large volume of a protic solvent such as water, then it is not necessary to purify the aprotic solvent extensively before use. This is a particularly important consideration when employing a method of HNS recovery involving the quenching of the reaction in an aqueous (preferably acidified) solution, because it means that aprotic solvent recovery need only involved a partial distillation of the water from the aprotic solvent/aqueous solution mixture (after the HNS and other byproducts and reactants have been removed) before the aprotic solvent can be reused. This in turn means that energy savings can be made.

A further advantage of the use of a protic cosolvent, especially water or methanol, in the oxidation step is that it reduces the solubility of HNS in the reaction medium and causes some of the HNS to precipitate out during the course of the oxidation reaction rather than at the end of the reaction or after the reaction has been quenched in aqueous solution. A slow precipitation of HNS during the reaction rather than a rapid precipitation at or after the end of the reaction encourages the growth of relatively coarse rather than fine HNS crystals, so that the recovery of HNS by filtration is made easier. This is an advantage over the method of Shipp which frequently yields a very fine product which is very difficult to filter, because of the very low solubility of HNS in Shipp's reaction medium. Furthermore, the slow precipitation of HNS facilitates a continuous oxidation reaction hence the continuous rather than the batch production of HNS. This may be achieved by continuously removing (eg filtering) HNS from the reaction medium as it is formed, and at the same time continuously dissolving fresh DPE or TNT reactant in the reaction medium. Such a continuous HNS production technique would render unnecessary the subsequent recovery for reuse, after each batch preparation of HNS, of the basic salt, aprotic solvent, and DPE/TNT reactants though it would be desirable to cleanse the reaction medium of unwanted oxidation reaction byproducts from time to time. Because much of the HNS produced by continuous production would of course spend a considerable amount of time dissolved in the reaction medium before precipitating out, which is not the case when employing batch preparation techniques, this underlines the importance of the discovery by the present inventors that salts of di- and polyfunctional carboxylic acids decompose the HNS product much more slowly than do salts of monofunctional carboxylic acids.

Methods of preparing 2,2',4,4',6,6'-hexanitrostilbene (HNS) in accordance with the present invention will now be described by way of example only. In each example, the products of the reactants described were characterised by means of their nuclear magnetic resonance (nmr) spectra, and optically by means of their melting points, to conform their identity and measure their purity. The solvents used were all general laboratory grade reagents unless otherwise stated.

PRODUCTION OF HNS FROM DPE

Example 1

1.9 g ($2.212 \times 10^{-3}$ mole) of 1,2-dipicrylethane (DPE) was dissolved in 25 ml of dimethylsulphoxide (DMSO) at 20° C., and placed in a reaction vessel equipped with a stirrer. 0.64 g ($4.44 \times 10^{-3}$ mole) of the basic salt sodium benzoate was dissolved in a further 25 ml of DMSO at 25° C. The DPE solution within the vessel was stirred at 800 rpm, and at the same time the solution of the basic salt was slowly added. While maintaining the vessel was temperature at 25° C., stirring was continued and approximately 2 liters $s^{-1}$ of dry air was then pumped through the solution until after about 30 minutes a colour change occurred from an initial blue colour to red/brown. The reaction was then quenched by pouring into 100 ml water which had been acidified with 1 ml concentrated hydrochloric acid. The solution was allowed to stand for ten minutes before the precipitate was isolated.

After washing with distilled water, the precipitate was dried at 60° C. and weighed. The yield of the crude product was found to be 0.96 g, or 96 mole %. The crude product was washed with methanol to remove by-products, followed by acetone to remove any unreacted DPE. The remaining insoluble solid was found to be pure 2,2',4,4',6,6'-hexanitrostilbene (HNS), which was then dried and weighed. The yield of the HNS product was found to be 0.64 g, or 64 mole %. The acetone filtrate was stripped of solvent, and the solid product so obtained dried and weighed. This yielded 0.17 g, or 17 mole %, of unreacted DPE, from which it may be calcualted that the total amount of DPE converted to other water-insoluble byproducts amounted to 0.15 g, or 15 mole % DPE.

Example 2

The method of Example 1 was repeated using a total of 50 ml dimethylformamide (DMF) instead of DMSO as the solvent in the reaction vessel. The crude yield was found to have increased to 0.97 g or 97 mole %, and the yield of the HNS product increased to 0.68 g, or 68 mole %. The yield of unreacted DPE was found to be 0.05 g, or 5 mole %, and thus the amount of DPE converted to other water-unsoluble byproducts was 0.24 g, or 24 mole %.

Example 3

The method of Example 1 was repeated using 0.36 g ($4.4 \times 10^{-3}$ mole) of sodium acetate in the reaction vessel, in place of the sodium benzoate. The crude yield from the reaction was found to be 0.96 g, or 96 mole % and the yield of pure HNS was 0.80 g, or 80 mole %. 8 mole % (0.08 g) of unreacted DPE was recovered, hence the conversion of DPE to water-insoluble by-product was 0.08 or 18 mole % of the original.

Example 4

The method of Example 3 was repeated using a total of 50 ml DMF instead of DMSO as the solvent in the reaction vessel. The crude yield was found to be 94 mole %, and the yield of pure HNS 81 mole %, with no unreacted DPE being recovered. 13 mole % DPE was therefore converted to water-insoluble by-products during the reaction.

Example 5

The method of Example 1 was repeated using 0.37 g ($4.4 \times 10^{-3}$ mole) of potassium formate in the reaction vessel, in place of the sodium benzoate. The crude yield from the reaction was found to be 96% mole % and the yield of pure HNS 84 mole %, with 4 mole % (0.4 g) of unreacted DPE being recovered by acetone washing and stripping. 8 mole % (0.08 g) DPE was therefore converted to water-insoluble by-products during the reaction.

Example 6

The method of Example 5 was repeated using a total of 50 ml DMF instead of DMSO as the solvent in the reaction vessel. The crude yield from the reaction was found to be 94 weight %, and the yield of pure HNS 81 mole %, with no unreacted DPE being recovered. 13 mole % (0.13 g) DPE was therefore converted to water-insoluble by-products during the reaction.

Example 7

The method of Example 1 was repeated, using only 0.23 g ($0.5 \times 10^{-3}$ mole) of DPE as the reaction substrate, 0.02 g ($2.4 \times 10^{-4}$ mole) of potassium formate as the catalyst in place of sodium benzoate, and 50 ml Analar (registered Trade Mark) Grade hexamethylphosphoramide (HMPA) as the solvent instead of DMSO. Furthermore, instead of pumping air through the solution, the reaction mixture was maintained under an atmosphere of dry oxygen, with vigorous stirring to effect contact between the gas and the solution.

The yield of pure HNS from the reaction was found to be 39 mole %, with 52 mole % of unreacted DPE being recovered by acetone washing and stripping. The crude product was found to contain 5% by weight of water-insoluble products other than DPE and HNS.

Example 8

The method of Example 7 was repeated using 0.04 g ($4.8 \times 10^{-4}$ mole) of potassium formate catalyst in the reaction vessel. The yield of pure HNS was found to have increased to 71 mole %, with a corresponding reduction in the amount of unreacted DPE to 20 mole %, though an increase to 7% by weight of water-insoluble products other than DPE and HNS was observed in the crude product.

Example 9

The method of Example 7 was repeated using 0.08 g ($9.6 \times 10^{-4}$ mole) of potassium formate catalyst, which resulted in a still further increase in the yield of pure HNS to 86 mole %. No unreacted DPE was recovered. The crude product contained 8% by weight of water-insoluble products other than HNS and DPE.

Example 10

The method of Example 7 was repeated using 0.12 g ($14.5 \times 10^{-4}$ mole) of potassium formate catalyst. The reaction yielded 84 mole % of HNS and no unreacted DPE, and the crude product contained 11% by weight of water-insoluble products other than HNS.

Example 11

The method of Example 1 was repeated using 0.38 g ($0.84 \times 10^{-3}$ mole) of DPE substrate, 0.23 g ($1.6 \times 10^{-3}$ mole) of sodium benzoate catalyst, and an especially purified DMSO.

The purification of the DMSO involved drying over a 4A molecular sieve for 48 hours, and distilling twice under reduced pressure. Furthermore, as with Examples 7 to 10 inclusive, the reaction mixture was maintained under an atmosphere of dry oxygen with vigorous mixing to effect liquid/gas contact, rather than pumping dry air through the solution.

The reaction yielded 71 mole % of pure HNS having a melting point of 315° C., and 27 mole % of unreacted DPE, from which it may be calculated that only 2 mole % of DPE was converted to other byproducts. No water-insoluble byproducts other than HNS and DPE were recovered from the crude product.

Example 12

The method of Example 11 was repeated using 0.37 g ($2.6 \times 10^{-3}$ mole) of sodium benzoate catalyst. The yield of pure HNS increased to 96 mole %, with no unreacted DPE being recovered. The melting point of the pure HNS was measured at 315° C. The crude product contained 2% by weight of water-insoluble products other than HNS.

Example 13

The method of Example 11 was repeated using 0.13 g ($1.6 \times 10^{-3}$ mole) of sodium acetate in place of the sodium benzoate catalyst. A yield of 91 mole % pure HNS having a melting point of 314° C. was produced from the reaction, and no unreacted DPE was recovered. The crude product was found to contain 8% by weight of water-insoluble products other than HNS.

Example 14

The method of Example 13 was repeated using 0.20 g ($2.4 \times 10^{-3}$ mole) of sodium acetate catalyst. A 90 mole % yield of pure HNS having a melting point of 314° C. was produced by the reaction. No unreacted DPE was recovered, but the crude product did contain 8% by weight of water-insoluble products other than HNS.

Example 15

The method of Example 11 was repeated using 0.13 g ($1.6 \times 10^{-3}$ mole) of potassium formate in place of the sodium benzoate catalyst. A yield of 94 mole % pure HNS having a melting point of 315° C. was produced by the reaction. Again, no unreacted DPE was recovered, but the crude product did contain 3% by weight of other water-insoluble byproducts.

Example 16

The method of Example 15 was repeated using 0.20 g ($2.4 \times 10^{-3}$ mole) of potassium formate catalyst. A 94 mole % yield of pure HNS (MP 315° C.) was again produced and with no unreacted DPE, but the amount of other water-insoluble byproducts in the crude product was found to have increased to 5% by weight.

Example 17

The method of Example 15 was repeated using 0.07 g ($0.84 \times 10^{-3}$ mole) of potassium formate catalyst. The yield of HNS (MP 315° C.) was found to have dropped to only 69 mole %, with 22 mole % being recovered as unreacted DPE from acetone washing and stripping. The crude product contained 4% by weight of other water-insoluble by-products.

Example 18

DPE (0.5 g, $1.106 \times 10^{-3}$ mole) was dissolve in dry DMSO (30 ml at 25° C.) and placed in a reaction vessel equipped with a stirrer. The atmosphere in the vessel, above the DMSO solution, was flushed with dry oxygen whilst the mixture was stirred at 800 revolutions per minute (rpm). After approximately 10 minutes, distilled water (0.05 ml) was injected into the reaction mixture. After a further five minutes, the pressure of oxygen in the reaction vessel was adjusted to atmosphere pressure, sodium benzoate (0.318 g, $2.2 \times 10^{-3}$ mole) was added to the solution, and the reaction vessel was then sealed. The reaction was allowed to continue in the presence of excess oxygen above the solution and whilst maintaining stirring and maintaining temperature at 25° C., until after about one hour the colour of the solution changed from an initial blue to red/brown. Quenching was then effected by pouring the solution into water (100 ml) which had been acidified with concentrated hydrochloric acid (1 ml). The mixture was allowed to stand for 10 minutes before the precipitate was isolated. After the washing with distilled water this crude product was dried and weighed so that crude product yield could be estimated. It was then purified by washing with methanol to remove water-insoluble byproducts, followed by acetone to remove any unreacted DPE. The residual, insoluble material remaining after this stage was pure HNS. This was dried and weighed so that HNS yield could be estimated. The amount of unreacted DPE was measured by stripping the acetone filtrate and drying and weighing the resulting solid residue.

Examples 19 to 25

The method of Examples 18 was repeated except that the amount of distilled water, added approximately 10 minutes after beginning the reaction procedure, was varied.

The results for each of the Examples 18 to 25 in terms of the length of time taken for the colour of the solution to change from blue to red brown (indicating the end point of the reaction) and in terms of product yields are given in Table 1 below.

TABLE 1

| Example | amount of H₂O ml | moles | reaction time (hours) | yield of HNS (mole %) | yield of other materials* (mole %) | unreacted DPE recovered (mole %) |
|---|---|---|---|---|---|---|
| 18 | 0.05 | $2.8 \times 10^{-3}$ | 1 | 90 | 6 | — |
| 19 | 0.18 | $1 \times 10^{-2}$ | 1 | 86 | 4 | — |
| 20 | 0.36 | $2 \times 10^{-2}$ | 1 | 92 | 6 | — |
| 21 | 1.80 | $1 \times 10^{-1}$ | 1 | 91 | 7 | — |
| 22 | 3.60 | $2 \times 10^{-1}$ | 1 | 94 | 5 | — |
| 23 | 5.00 | $2.7 \times 10^{-1}$ | 1 | 94 | 4 | — |
| 24 | 7.00 | $3.8 \times 10^{-1}$ | 4 | 93 | 2 | — |

TABLE 1-continued

| Example | amount of H₂O ml | moles | reaction time (hours) | yield of HNS (mole %) | yield of other materials* (mole %) | unreacted DPE recovered (mole %) |
|---|---|---|---|---|---|---|
| 25 | 10.00 | 5.5 × 10⁻¹ | 24 | — | — | 100 |

*ie reaction by-product materials which are insoluble in acidified water but soluble in methanol.

Example 26

DPE (0.5 g, 1.106×10⁻³ mole) was dissolved in dry DMSO (30 ml at 25° C.) and placed in a reaction vessel equipped with a stirrer. The atmosphere in the vessel, above the reaction mixture, was flushed with dry oxygen whilst the solution was stirred at 800 rpm. After approximately ten minutes, the pressure of oxygen in the vessel was adjusted to atmospheric pressure, sodium benzoate (0.318 g, 2.2×10⁻³ mole) was added, and the reaction vessel was sealed. The reaction was allowed to continue in the presence of oxygen above the solution whilst maintaining stirring and maintaining the vessel temperature at 25° C., until after about 90 minutes the solution changed in colour from an initial blue to red/brown. Quenching was then effected by pouring it into water (100 ml) which had been acidified with concentrated hydrochloric acid (1 ml). The mixture was allowed to stand for 10 minutes before the precipitate was isolated. After washing with distilled water this material was dried and weighed so that crude product yield could be estimated. The crude product thus obtained was purified by washing with methanol to remove water-insoluble byproducts, followed by acetone to remove any unreacted DPE. The residual insoluble material was pure HNS. This was dried and weighed so that HNS yield could be estimated. The amount of unreacted DPE was measured by stripping the acetone filtrate and drying and weighing the resulting solid residue.

Examples 27 to 30

The method of Example 26 was repeated except that various dry DMSO/acetone mixtures (30 ml at 25° C.) were employed as the solvent instead of DMSO alone.

The results in terms of the length of time taken for the colour of the solution to change from blue to red/brown (indicating the end point of the reaction) and in terms of product yields, are given in Table 2 below.

TABLE 2

| Example | DMSO/ Acetone ratio (v/v) | reaction time (minutes) | yield of HNS (mole %) | yield of other materials* (mole %) | unreacted DPE recovered (mole %) |
|---|---|---|---|---|---|
| 26 | 100/0 | 60 | 91 | 6 | — |
| 27 | 75/25 | 90 | 60 | 20 | 5 |
| 28 | 50/50 | 90 | 51 | 32 | 12 |
| 29 | 25/75 | 120 | 16 | 24 | 56 |
| 30 | 0/100 | 240 | — | — | 100 |

*ie reaction byproduct materials which are insoluble in acidified water but soluble in methanol.

Examples 31-26

The methods of Examples 26-30 were repeated except that various dry DMSO/methanol mixtures (30 ml at 25° C.) were used instead of DMSO/acetone mixtures, and 0.29 g (2.0×10⁻³ mole) sodium benzoate was used in each method instead of 0.318 g. The results for each of the Examples 31 to 36 in terms of reaction time and product yields are given in Table 3 below.

TABLE 3

| Example | DMSO methanol ratio (v/v) | reaction time (minutes) | yield of HNS (mole %) | yield of other materials* (mole %) | unreacted DPE recovered (mole %) |
|---|---|---|---|---|---|
| 31 | 100/0 | 60 | 90 | 7 | — |
| 32 | 90/10 | 70 | 92 | 4 | — |
| 33 | 75/25 | 90 | 90 | 6 | 10 |
| 34 | 50/50 | 120 | 20 | 1 | 76 |
| 35 | 25/75 | 240 | — | — | 98 |
| 36 | 0/100 | 240 | — | — | 100 |

*ie reaction byproduct materials which are insoluble in acidified water but soluble in methanol.

Examples 37-39

The method of Example 26 was repeated employing various quantities of ammonium formate as the base catalyst instead of sodium benzoate. In each of the Examples 37 to 39, the period of time taken for the color of the reacting solution to change from blue to red/brown was about 40 minutes. Product yields from each of the reactions performed in accordance with the methods of Examples 37 to 39 are given in Table 4 below.

TABLE 4

| Example | Quantity of base used (g) | Molar Ratio of base: DPE | yield of HNS (mole %) | yield of other materials* (mole %) | unreacted DPE recovered (mole %) |
|---|---|---|---|---|---|
| 37 | 0.073 | 1.1:1 | 74 | 15 | 0 |
| 38 | 0.13 | 1.9:1 | 82 | 16 | 0 |
| 39 | 0.3 | 4.4:1 | 79 | 18 | 0 |

*ie reaction byproduct materials which are insoluble in acidified water but soluble in methanol.

Example 40

The method of Example 26 was repeated 0.14 g (2.12×10⁻³ mole) lithium acetate as the base catalyst rather than sodium benzoate. The reaction mixture, once the reaction was completed as indicated by the characteristic solution colour change, yielded 0.42 g, or 84 mole %, of pure HNS product.

Example 41 to 45

The method of Example 26 was repeated employing various basic salts of dicarboxylic acids as the base catalyst rather than sodium benzoate. In each of the Examples 41 to 45, the reaction time taken to bring about the characteristic solution colour change from blue to red/brown was about 60 minutes. Product yields from each of the reactions performed in accordance with the methods of Examples 41 to 45 are given in Table 5 below.

TABLE 5

| Example | Base | Quantity of base used (g) | Molar ratio of base: DPE | yield of HNS (mole %) | yield of other materials* (mole %) | unreacted DPE recovered (mole %) |
|---|---|---|---|---|---|---|
| 41 | disodium oxalate | 0.15 | 1.2:1 | 89 | 6 | 0 |
| 42 | disodium oxalate | 0.30 | 2.4:1 | 92 | 7 | 0 |
| 43 | disodium succinate | 0.18 | 1.15:1 | 84 | 6 | 0 |
| 44 | disodium succinate | 0.36 | 2.3:1 | 91 | 8 | 0 |

TABLE 5-continued

| Example | Base | Quantity of base used (g) | Molar ratio of base: DPE | yield of HNS (mole %) | yield of other materials* (mole %) | unreacted DPE recovered (mole %) |
|---|---|---|---|---|---|---|
| 45 | disodium tartrate | 0.22 | 1.15:1 | 52 | | |

*ie reaction byproduct materials which are insoluble in acidified water but soluble in methanol.

Example 46

DPE (0.5 g, $1.106 \times 10^{-3}$ mole) was dissolved in dry DMSO (30 ml) and was placed in a reaction vessel equipped with a stirrer. The resulting solution was degassed by repeated freeze/pump/thaw cycles. The atmosphere in the vessel was then flushed with dry, oxygen-free nitrogen whilst the solution was thermostatted at 25° C. and stirred at 800 rpm. After approximately 10 minutes, the pressure of nigrogen in the vessel was adjusted to atmospheric pressure and to the solution was added potassium formate (0.08 g, $1.0 \times 10^{-3}$ mole and the oxidising agent tetrachloro-p-benzoquinone (0.27 g). The reaction was allowed to continue for 1 hour under nitrogen whilst maintaining stirring and maintaining the vessel temperature at 25° C., after which time the reaction was deemed to be completed (no colour change was observed to signify the completion of the reaction as occurs when $O_2$ is used to oxidize the DPE). Quenching was then effected by pouring the solution in water (100 ml) which had been acidified with concentrated hydrochloric acid (1 ml). The mixture was allowed to stand for 10 minutes before the precipitate was isolated. After washing with distilled water this crude product was dried and weighed so that crude product yield could be estimated. It was then purified by washing with methanol to remove water-insoluble byproducts, followed by acetone to remove any unreacted DPE. The residual, insoluble material remaining after this stage was pure HNS. This was dried and weighed so that HNS yield could be estimated. The amount of unreacted DPE was measured by stripping the acetone filtrate and drying and weighing the resulting solid residue.

Examples 47 to 49

The method of Example 46 was repeated in three further Examples using different quantities of potassium formate base.

The results for each of the Examples 46 to 49 in terms of product yields are given in Table 6 below.

TABLE 6

| Example | Quantity of base used (g) | Molar ratio of base: DPE | yield of HNS (mole %) | yield of other materials* (mole %) | unreacted DPE recovered (mole %) |
|---|---|---|---|---|---|
| 46 | 0.08 | 0.9:1 | 39 | 8 | 51 |
| 47 | 0.16 | 1.7:1 | 76 | 11 | 6 |
| 48 | 0.25 | 2.7:1 | 64. | 18 | 1 |
| 49 | 0.32 | 3.5:1 | 64 | 24 | 0 |

*ie reaction byproduct materials which are insoluble in acidified water but soluble in methanol.

Examples 50 to 52

The method of Example 46 was requested in three yet further Examples using HMPA solvent (30 ml) instead of DMSO, 0.09 g ($1 \times 10^{-3}$ mole) sodium acetate instead of potassium formate, and various organic oxidants. The reaction was allowed to continue for 2 hours rather than one, though again no colour change was observed to signify that the reaction was completed. The results for each of the Examples 50 to 52 in terms of product yields are given in Table 7 below.

TABLE 7

| Example | Oxidant | Quantity of Oxidant used (g) | yield of HNS (mole %) | yield of other materials* (mole %) | unreacted DPE recovered (mole %) |
|---|---|---|---|---|---|
| 50 | tetrachloro-p-benzoquinone | 0.27 | 24 | 31 | 42 |
| 51 | 2,3-dichloro-5,6-dicyano-1,4-benzoquinone | 0.25 | 32 | 30 | 31 |
| 52 | p-benzoquinone | 0.12 | 18 | 34 | 44 |

*ie reaction byproduct materials which are insoluble in acidified water but soluble in methanol.

PRODUCTION OF HNS FROM TNT

Example 53

2,4,6-trinitrolouene (TNT) (0.5 g, $2.203 \times 10^{-3}$ mole) was dissolved in DMSO (30 ml, at 25° C.) and placed in a reaction vessel equipped with a stirrer. The atmosphere in the vessel, above the reaction mixture, was flushed with dry oxygen whilst the solution was stirred (800 rpm). After approximately ten minutes, the pressure of oxygen in the vessel was adjusted to atmospheric pressure, sodium benzoate (0.632 g, $4.4 \times 10^{-3}$ mole) was added, and the vessel then sealed. The reaction was allowed to continue, in the presence of excess oxygen in the vessel while maintaining stirring and maintaining the temperature at 25° C., until after about 90 minutes the solution changed in colour from an initial purple to red/brown. Quenching was then effected by pouring the solution into water (100 ml) which had been acidified with concentrated hydrochloric acid (1 ml). The mixture was allowed to stand for 30 minutes before the precipitate was isolated. After washing with distilled water this material was dried and weighed. The crude product thus obtained was washed first with methanol, then with acetone. The residual insoluble material was pure HNS. This was dried and weighed so that HNS yield could be estimated. The acetone filtrate was stripped of solvent and the solid product so obtained dried and weighed. This product was identified as DPE. Any unreacted TNT was recrystallised from the methanol filtrate and dried and weighed.

Examples 54 to 57

The method of Example 53 was repeated using various different molar concentrations of the sodium benzoate base in the reaction mixture. In each of these further Examples, the time taken for the colour change to take place in the reaction mixture was found to be about 90 minutes.

The results for each of the Examples 53 to 57 in terms of product yields are given in Table 8 below.

TABLE 8

| Example | Quantity of base | Molar ratio of base: TNT | yield of HNS (mole %) | yield of DPE (mole %) | yield of other materials* (mole %) | unreacted TNT recovered (mole %) |
|---|---|---|---|---|---|---|
| 53 | 0.632 | 2:1 | 15 | 10 | 28 | 49 |
| 54 | 0.948 | 3:1 | 43 | 12 | 31 | 10 |
| 55 | 1.264 | 4:1 | 61 | 4 | 32 | 1 |
| 56 | 1.58 | 5:1 | 60 | 0 | 38 | 0 |
| 57 | 1.896 | 6:1 | 49 | 0 | 46 | 0 |

*ie reaction byproduct materials which are insoluble in acidified water but soluble in methanol.

Examples 58 to 62

The method of Example 53 was repeated using various different molar concentrations of potassium formate (molecular weight: 84) instead of sodium benzoate as the base catalyst. In each of these Examples, the time taken for the purple to red/brown colour change to take place was about 90 minutes. The results for each of the Examples 58 to 62 in terms of product yields are given in Table 9 below.

TABLE 9

| Example | Quantity of base used (g) | Molar ratio of base: TNT | yield of HNS (mole %) | yield of DPE (mole %) | yield of other materials* (mole %) | unreacted TNT recovered (mole %) |
|---|---|---|---|---|---|---|
| 58 | 0.374 | 2:1 | 18 | 12 | 24 | 41 |
| 59 | 0.561 | 3:1 | 42 | 14 | 29 | 14 |
| 60 | 0.748 | 4:1 | 62 | 8 | 38 | 0 |
| 61 | 0.935 | 5:1 | 51 | 0 | 44 | 0 |
| 62 | 1.122 | 6:1 | 46 | 0 | 52 | 0 |

*ie reaction byproduct materials which are insoluble in acidified water but soluble in methanol.

Examples 63 to 68 (comparative Examples)

For the purpose of comparison with the method of the present invention, the method of Example 53 was repeated using various different molar concentrations of a strong base, potassium hydroxide, instead of the weak base sodium benzoate. In each of these Examples, a colour change from purple to red/brown in the reaction mixture occurred after about 90 minutes. The results for each of the comparative Examples 63 to 68 in terms of product yields.

TABLE 10

| Example | Quantity of base used (g) | Molar ratio of base: TNT | yield of HNS (mole %) | yield of DPE (mole %) | yield of other materials* (mole %) | unreacted TNT recovered (mole %) |
|---|---|---|---|---|---|---|
| 63 | 0.123 | 1:1 | 0 | 0 | 20 | 68 |
| 64 | 0.246 | 2:1 | 0 | 2 | 22 | 63 |
| 65 | 0.369 | 3:1 | 10 | 12 | 40 | 32 |
| 66 | 0.498 | 4:1 | 14 | 7 | 71 | 0 |
| 67 | 0.616 | 5:1 | 14 | 2 | 80 | 0 |
| 68 | 0.739 | 6:1 | 10 | 0 | 86 | 0 |

*ie reaction byproduct materials which are insoluble in acidified water but soluble in methanol.

The above Table 10 illustrates the poor yields of HNS and high hields of unwanted byproducts produced when using a strong base catalyst as compared with product yields using the weak base catalyst in accordance with the present invention as illustrated in the above Tables 8 and 9.

Examples 69 to 74

The method of Example 60 (using 0.748 g of potassium formate base catalyst) was repeated using various 30 ml mixtures of DMSO and DMF instead of 30 ml of pure DMSO. In each of these Examples, the time taken for the purple to red/brown colour change to take place was about 90 minutes. The result for each of the Examples 69 to 74 in terms of product yields are given in Table 11 below.

TABLE 11

| Example | DMF/DMSO ratio (v/v) | yield of HNS (mole %) |
|---|---|---|
| 69 | 10/90 | 58 |
| 70 | 25/75 | 59 |
| 71 | 50/50 | 58 |
| 72 | 75/25 | 51 |
| 73 | 90/10 | 50 |
| 74 | 100/0 | 48 |

*ie reaction byproduct materials which are insoluble in acidified water but soluble in methanol.

We claim:

1. A method of preparing 2,2',4,4',6,6'-hexanitrostilbene (HNS) which comprises the steps of
   (a) oxidizing to a nitrated organic reactant, selected from 1,2-dipicrylethane (DPE) and 2,4,6-trinitrotoluene (TNT), to HNS with an oxidizing agent, said oxidation being performed in an aprotic solvent having dissolved therein a soluble base selected from the group consisting of salts of monocarboxylic acids, salts of dicarboxylic acids, and salts of polycarboxylic acids, and
   (b) recovering the HNS from the aprotic solvent, provided that when DPE is oxidized and the base is a salt of a monocarboxylic acid, the molar ratio of DPE to base in the aprotic solvent is between 1:1 and 1:6.

2. A method according to claim 1 wherein the soluble base is selected from the group consisting of salts of aliphatic monocarboxylic acids and salts of aromatic monocarboxlyic acids.

3. A method according to claim 2 wherein the monocarboxylic acids are selected from the group consisting of formic acid, acetic acid and benzoic acid.

4. A method according to claim 1 wherein the soluble base is selected from the group consisting of salts of aliphatic dicarboxylic acids, salts of aromatic dicarboxylic acids, salts of aliphatic polycarboxylic acids and salts of aromatic polycarboxylic acids.

5. A method according to claim 1 wherein said soluble base is selected from the group consisting of alkali metal salts and ammonium salts.

6. A method according to claim 1 wherein the oxidizing agent is selected from the group consisting of free oxygen, hydrogen peroxide, tetrachloro-p-benzoquinone, 2,3-dichloro-5,6-cyano-1,4-benzonquinone and p-benzoquinone.

7. A method according to claim 1 wherein the aprotic solvent is selected from the group consisting of dimethylformamide, dimethylsulphoxide, and hexamethylphosphoramide.

8. A method according to claim 1 wherein the reaction medium of step (a) further comprises between 0 and 30% by volume of a protic solvent.

9. A method according to claim 8 wherein the reaction medium of step (a) further comprises between 0 and 20% by volume of a protic solvent.

10. A method according to claim 9 wherein the reaction medium of step (a) further comprises between 0 and 15% by volume of a protic solvent.

11. A method according to claim 10 wherein the reaction medium of step (a) further comprises between 0 and 10% by volume of a protic solvent.

12. A method according to claim 8 wherein the protic solvent is selected from the group consisting of alkanols and water.

13. A method according to claim 12 wherein the protic solvent comprises methanol.

14. A method according to claim 1 wherein the nitrated organic reactant is DPE, the base is a salt of a dicarboxylic acid or a polycarboxylic acid, and the molar ratio of DPE to base in the aprotic solvent is between 1:0.5 and 1:10.

15. A method according to claim 1 wherein the nitrated organic reactant is DPE, the base is a salt of a monocarboxylic acid, and the molar ratio of DPE to base in the aprotic solvent is between 1:1 and 1:6.

16. A method according to claim 1 wherein the nitrated organic reactant is oxidised at a temperature between 15° C. and 50° C.

17. A method of preparing 2,2',4,4',6,6'-hexanitrostilbene (HNS) which comprises the step of:
   (a) oxidizing 2,4,6-trinitrotoluene (TNT) to HNS with an oxidizing agent, said oxidation being performed in an aprotic solvent having dissolved therein a soluble base selected from the group consisting of salts of monocarboxylic acids, salts of dicarboxylic acids and salts of polycarboxylic acids, and
   (b) recovering HNS from the aprotic solvent.

18. A method according to claim 17 wherein the soluble base is selected from the group consisting of salts of aliphatic monocarboxylic acids and salts of aromatic monocarboxylic acids.

19. A method according to claim 18 wherein the monocarboxylic acids are selected from the group consisting of formic acid, acetic acid and benzoic acid.

20. A method according to claim 17 wherein the soluble base is selected from the group consisting of salts of aliphatic dicarboxylic acids, salts of aromatic dicarboxylic acids, salts of aliphatic polycarboxylic acids and salts of aromatic polycarboxylic acids.

21. A method according to claim 17 wherein the soluble base is selected from the group consisting of alkali metals and ammonium salts.

22. A method according to claim 17 wherein the oxidizing agent is selected from the group consisting of free oxygen, hydrogen peroxide, tetrachloro-p-benzoquinone, 2,3-dichloro-5,6-cyano-1,4-benzoquinone and p-benzoquinone.

23. A method according to claim 17 wherein the aprotic solvent is selected from the group consisting of dimethylformamide, dimethylsulphoxide, and hexamethylphosphoramide.

24. A method according to claim 17 wherein the reaction medium of step (a) further comprises between 0 and 30% by volume of a protic solvent.

25. A method according to claim 24 wherein the reaction medium of step (a) further comprises between 0 and 20% by volume of a protic solvent.

26. A method according to claim 25 wherein the reaction medium of step (a) further comprises between 0 and 15% by volume of a protic solvent.

27. A method according to claim 26 wherein the reaction medium of step (a) further comprises between 0 and 10% volume of a protic solvent.

28. A method according to claim 24 wherein the protic solvent is selected from the group consisting of alkanols and water.

29. A method according to claim 28 wherein the protic solvent comprises methanol.

30. A method according to claim 17 wherein the molar ratio of TNT to base within the aprotic solvent is is between 1:0.5 and 1:10.

31. A method according to claim 30 wherein the molar ratio of TNT to base in the aprotic solvent is between 1:1 and 1:6.

32. A method according to claim 17 wherein the TNT is oxidized at a temperature between 15° C. and 50° C.

* * * * *

UNITED STATES PATENT AND TRADEMARK OFFICE
CERTIFICATE OF CORRECTION

PATENT NO. : 4,626,606

DATED : December 2, 1986

INVENTOR(S) : Henry C. DUFFIN et al

It is certified that error appears in the above-identified patent and that said Letters Patent is hereby corrected as shown below:

In Column 14, line 3 of Claim 1, delete "to".

Signed and Sealed this

Thirty-first Day of March, 1987

Attest:

DONALD J. QUIGG

Attesting Officer     Commissioner of Patents and Trademarks